(12) United States Patent
Roschak et al.

(10) Patent No.: US 10,314,619 B2
(45) Date of Patent: Jun. 11, 2019

(54) REMOTELY ADJUSTABLE INTERACTIVE BONE RESHAPING IMPLANT

(71) Applicant: NuVasive Specialized Orthopedics, Inc., San Diego, CA (US)

(72) Inventors: Edmund J. Roschak, Aliso Viejo, CA (US); Thomas B. Buford, Aliso Viejo, CA (US)

(73) Assignee: NuVasive Specialized Orthopedics, Inc., San Diego, CA (US)

( * ) Notice: Subject to any disclaimer, the term of this patent is extended or adjusted under 35 U.S.C. 154(b) by 68 days.

(21) Appl. No.: 15/521,025

(22) PCT Filed: Oct. 22, 2015

(86) PCT No.: PCT/US2015/057010
§ 371 (c)(1),
(2) Date: Apr. 21, 2017

(87) PCT Pub. No.: WO2016/065205
PCT Pub. Date: Apr. 28, 2016

(65) Prior Publication Data
US 2017/0333080 A1 Nov. 23, 2017

Related U.S. Application Data

(60) Provisional application No. 62/067,937, filed on Oct. 23, 2014.

(51) Int. Cl.
*A61B 17/00* (2006.01)
*A61B 17/58* (2006.01)
(Continued)

(52) U.S. Cl.
CPC .......... *A61B 17/68* (2013.01); *A61B 17/7016* (2013.01); *A61B 17/7216* (2013.01);
(Continued)

(58) Field of Classification Search
CPC . A61B 17/68; A61B 17/7016; A61B 17/7216; A61B 5/01; A61B 5/02055;
(Continued)

(56) References Cited

U.S. PATENT DOCUMENTS

| 5,156,605 A | 10/1992 | Pursley et al. |
| 7,559,951 B2 * | 7/2009 | DiSilvestro ............... A61F 2/36 623/23.16 |

(Continued)

OTHER PUBLICATIONS

International Search Report and Written Opinion for application serial No. PCT/US2015/057010 dated Jan. 8, 2016.

*Primary Examiner* — Pedro Philogene

(57) ABSTRACT

According to some embodiments, systems and methods for reshaping bone are provided. The systems may include an implant body, an actuator coupled to the implant body, a sensor configured to detect a parameter indicative of a biological condition, a transceiver, and a controller. The transceiver may be configured to transmit data associated with the parameter to an external remote control and receive instructions from the external remote control. Finally, the controller is configured to move the actuator in response to the instructions from the external remote control, wherein the actuator adjusts the implant body. The methods may include measuring a parameter indicative of a biological condition; transmitting data associated with the parameter from the implantable device to an external remote control; transmitting instructions from the external remote control to the implantable device; and actuating the bone growth device in response to the instructions from the external remote control.

30 Claims, 11 Drawing Sheets

(51) Int. Cl.
*A61B 17/70* (2006.01)
*A61B 17/72* (2006.01)
*A61B 5/00* (2006.01)
*A61B 17/68* (2006.01)
*A61B 5/01* (2006.01)
*A61B 5/0205* (2006.01)
*A61B 5/026* (2006.01)
*A61B 5/053* (2006.01)
*A61B 5/107* (2006.01)
*A61B 5/145* (2006.01)

(52) U.S. Cl.
CPC ............... *A61B 5/01* (2013.01); *A61B 5/026* (2013.01); *A61B 5/02055* (2013.01); *A61B 5/053* (2013.01); *A61B 5/1072* (2013.01); *A61B 5/14539* (2013.01); *A61B 5/4504* (2013.01); *A61B 5/4509* (2013.01); *A61B 5/4836* (2013.01); *A61B 5/686* (2013.01); *A61B 2017/00022* (2013.01); *A61B 2017/00402* (2013.01); *A61B 2017/00407* (2013.01); *A61B 2017/00867* (2013.01); *A61B 2017/681* (2013.01); *A61B 2560/0475* (2013.01); *A61B 2562/0261* (2013.01)

(58) Field of Classification Search
CPC ....... A61B 5/026; A61B 5/053; A61B 5/1072; A61B 5/14539; A61B 5/4504; A61B 5/4509; A61B 5/4836; A61B 5/686; A61B 2017/00022; A61B 2017/00402; A61B 2017/00407; A61B 2017/00867; A61B 2017/681; A61B 2560/0475; A61B 2562/0261
USPC ... 606/62, 63, 64, 68, 90, 105, 52–59, 86 R; 623/22.4–23.17, 23.44–23.49, 16.11, 623/18.11
See application file for complete search history.

(56) References Cited

U.S. PATENT DOCUMENTS

| | | | |
|---|---|---|---|
| 8,486,070 B2 * | 7/2013 | Morgan | A61B 5/0031 606/62 |
| 2007/0173837 A1 * | 7/2007 | Chan | A61B 17/66 606/63 |
| 2011/0196435 A1 * | 8/2011 | Forsell | A61B 17/68 606/86 R |
| 2011/0319755 A1 * | 12/2011 | Stein | A61B 5/0031 600/437 |

* cited by examiner

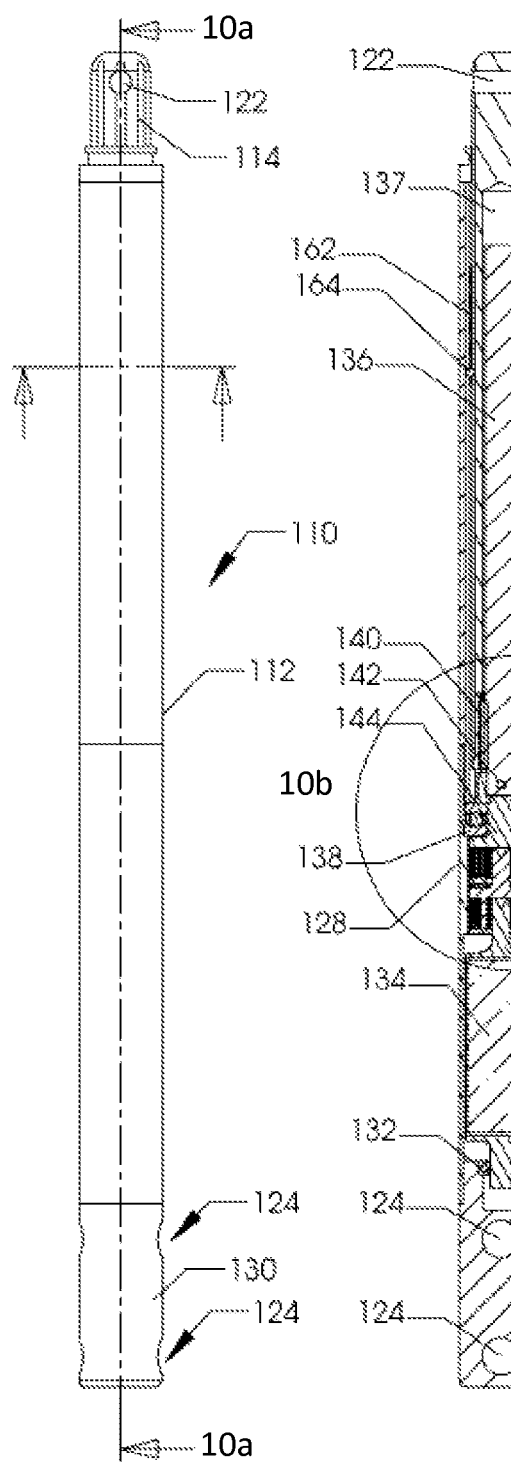
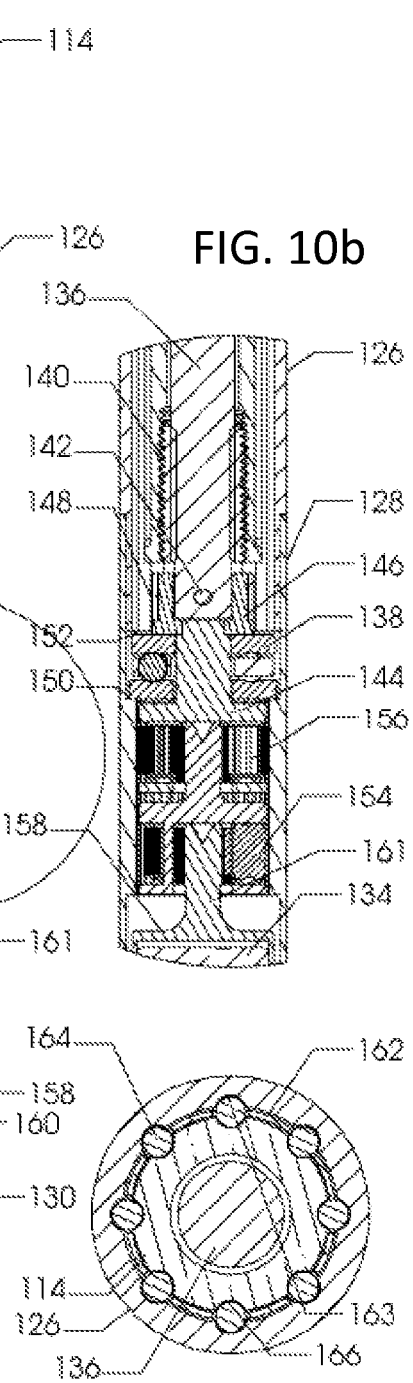

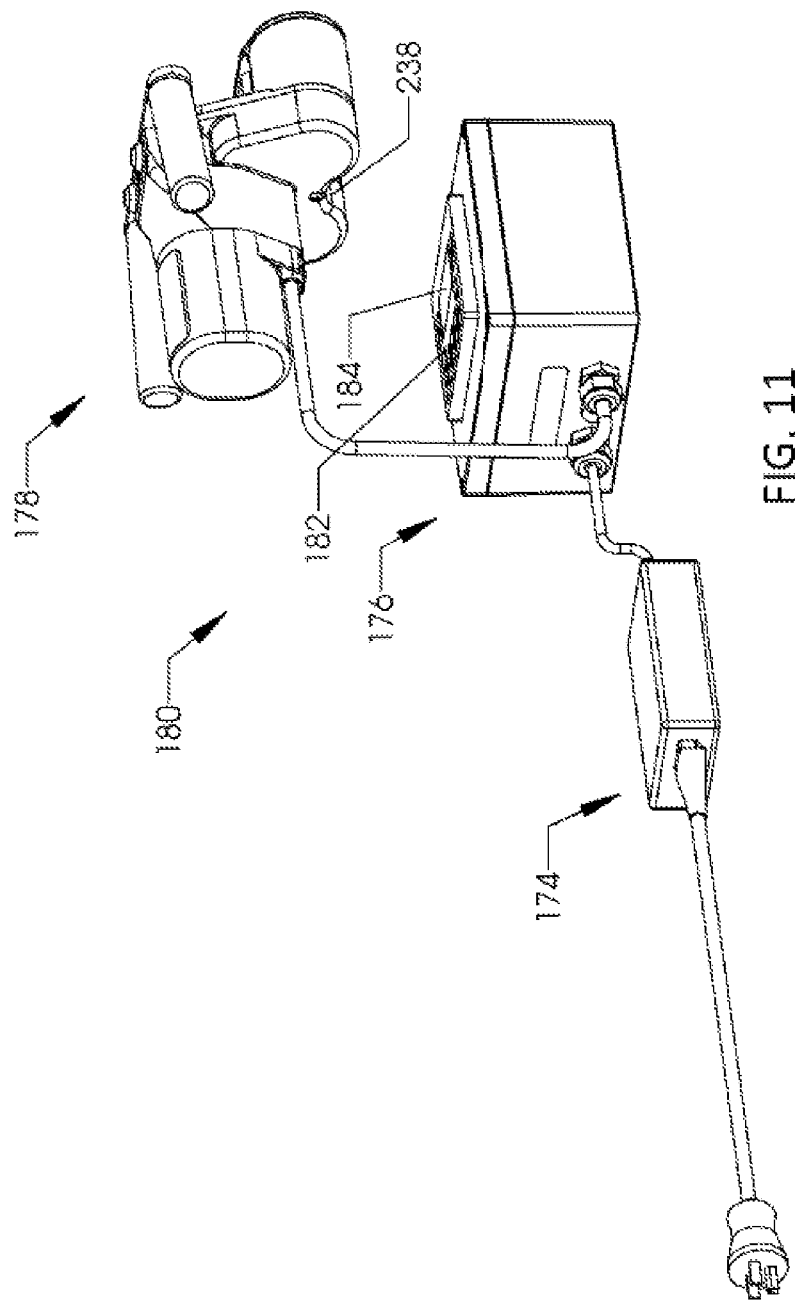

REMOTELY ADJUSTABLE INTERACTIVE BONE RESHAPING IMPLANT

BACKGROUND

The present invention relates to orthopaedic methods and devices for the gradual modification of bones or correction of bone deformities. In particular, the present invention relates to a variety of bone reshaping devices configured to perform procedures, including the lengthening of a bone, the shortening of a bone, the healing of a fracture, the changing of a bone angle, the rotation of a bone, the adjustment of the curvature or torsion of a bone, the realignment or repositioning of a joint or a vertebra, the reforming or supporting of the shape of the spinal column, or combinations thereof, all of which are considered species of "reshaping" as used herein. More specifically, the present invention relates to methods and systems concerning bone reshaping devices that can be externally adjusted based on measured parameters indicative of biological conditions.

External fixation devices, adjustable in length and angular attitude, are commonly utilized for correcting certain angular and longitudinal defects of long bones of limbs. Such fixation devices essentially comprise clamps which hold groups of bone screws inserted in the portions of the bone affected by defects, such clamps being slidably mounted on elements or guides longitudinally positionable externally to the limb to be treated.

The correction is normally carried out gradually with the aid of compression/distraction devices which act on the mobile clamps while the bone callous regenerates itself permitting its manipulation until the desired correction is obtained.

For example, in limb lengthening, the bone is commonly surgically divided into two segments, and wires and half pins are inserted into bone segments above and below the surgical bone cut and are attached to rings of a rigid framework interconnected by struts or telescopic connection rods. The rigid framework is used to gradually push the two bone segments apart longitudinally over a period of time (e.g., one millimeter a day). This allows the bone to gradually form in the gap between bone segments created by this distraction technique. Once the desired amount of lengthening is achieved 5-6 cm), the external apparatus is stabilized into a fixed position and left on the bone segments until complete mineralization of the newly formed bone occurs 3-6 months, depending on the nature of pathology and amount of lengthening).

Similarly, in deformity correction, the bone is surgically divided usually at the apex of the deformity) into two segments, and wires and half pins are inserted into bone segments above and below the surgical bone cut and attached to rings of a rigid framework. Opposite rings of the rigid framework are connected together by threaded rods with attached uni-planar or multi-planar hinges and angular distracters that are used to gradually push the two bone segments apart angularly over a period of time.

The use of such external fixation devices can present certain disadvantages. The external fixator can be unwieldy, painful for the patient, and also subjects the patient to the risk of pin track infections, joint stiffness, loss of appetite, depression, cartilage damage, and other side effects. Having the external fixator in place also delays the beginning of rehabilitation. In some circumstances, the visibility of the external fixator can lead to patient embarrassment or insecurity.

In response to these shortcomings, the art developed implantable devices that could be positioned under the skin and/or in bones. These devices were designed to correct bone deformities by applying force to bones, including compressive forces to promote healing, distractive forces to promote lengthening, and angular forces to change the angle/curvature of bones. Some desirable aspects of these implantable devices were that they could apply steady forces over defined periods of time, did not have external wires or rods that could bother the patient or cause pain, had reduced risks of infections, and were not readily visible.

Yet, even these implantable devices could have limitations as well in some cases. For example, because of their location under the skin, some implants could be difficult for care providers to observe, monitor, and adjust. As such, additional surgical procedures would sometimes be performed to incrementally adjust an implant as therapeutically required. The additional surgical procedures exposed patients to increased risks of infection, longer healing times, injury, and increased pain.

In other cases, even where adjustments to implants could be made through the skin, the therapeutic effects of the implant could be less than optimal. Under-application of force could lead to poor bone reformation and/or require longer recovery times. Over-application of force could lead to injury, further bone deformation, and also longer recovery times. Moreover, frequent visits to see a practitioner for adjustments could be time consuming or otherwise inconvenient for a patient.

Thus, notwithstanding the efforts of the prior art, there remains a need for an improved technology for controlling implantable bone reshaping devices in order to improve their performance and efficacy.

SUMMARY

In accordance with one embodiment, a bone growth device is provided. The bone growth device comprises an implant body, an actuator, a sensor, a transceiver, and a controller. The actuator is coupled to the implant body. The sensor is configured to detect a measurable parameter indicative of a biological condition. The transceiver is configured to transmit data associated with the measureable parameter to an external remote control and receive instructions from the external remote control. Finally, the controller is configured to move the actuator in response to the instructions from the external remote control, wherein the actuator adjusts the implant body.

In accordance with another embodiment, an external remote control for a bone growth device is provided. The external remote control comprises a first transceiver, an input, and a controller. The first transceiver is configured to receive data associated with a measurable parameter from the bone growth device and to transmit instructions for the bone growth device. The input is for receiving care information from a care provider. Finally, the controller is configured to: 1) receive the data associated with a measurable parameter and care information; and 2) generate the instructions for the bone growth device based on at least one of the data associated with a measurable parameter and care information.

In accordance with another embodiment, a method for treating a patient using an implantable device is provided. The method comprises the steps of: measuring a measurable parameter indicative of a biological condition; transmitting data associated with the measureable parameter from the implantable device to an external remote control; transmitting instructions from the external remote control to the implantable device; and actuating the bone growth device in response to the instructions from the external remote control.

BRIEF DESCRIPTION OF THE DRAWINGS

The disclosed aspects will hereinafter be described in conjunction with the appended drawings, provided to illustrate and not to limit the disclosed aspects, wherein like designations denote like elements.

FIG. 9 is a side view of a hone reshaping device, adapted for axial lengthening and shortening.

FIG. 10a illustrates a longitudinal cross-section view of the device of FIG. 9, taken along lines 10a-10a.

FIG. 10b illustrates a detailed view of the lengthening device of FIG. 10a, from the area of circle 10b.

FIG. 11 illustrates an example external remote controller for wirelessly controlling and communicating with the implantable device of FIG. 8.

DETAILED DESCRIPTION

Various embodiments are described herein, which provide methods and systems related to bone reshaping devices that can be externally controlled and adjusted in response to parameters measured by the implant, to enable therapy to be optimized for each patient in response to measureable indicium of biological response obtained from the sensors on the implant.

It will be of course understood that various omissions, substitutions, and changes in the form and details of the alternatives illustrated can be made without departing from the spirit of the disclosure. Additionally, the various features and processes described herein can be used independently of one another, or can be combined in various ways. All possible combinations and subcombinations are intended to fall within the scope of this disclosure. Many of the alternatives described herein include similar components, and as such, these similar components can be interchanged in different aspects of the invention.

There has been a long felt need for implantable bone shaping devices that can be effectively and/or adaptively adjusted for therapy. The present disclosure describes a number of illustrative examples detailing how an implant may measure parameters of a patient indicative of a biological condition (e.g., osteogenesis), and interpret or display such information for further therapeutic treatment.

Examples of conditions contemplated as potentially treatable in accordance with the present invention include congenital deformities (birth defects), such as congenital short femur; fibular hemimelia (absence of the fibula, which is one of the two bones between the knee and the ankle); hemiatrophy (atrophy of half of the body); and Ollier's disease (also known as multiple endochondromatosis, dyschondroplasia, and endochondromatosis); developmental deformities, such as neurofibromatosis (a rare condition which causes overgrowth in one leg); and bow legs, resulting from rickets (rachitis) or secondary arthritis; post-traumatic injuries, such as growth plates fractures; malunion or non-union (When bones do not completely join, or join in a faulty position after a fracture); shortening and deformity; bone defects; infections and diseases, such as osteomyelitis (a bone infection, usually caused by bacteria); septic arthritis (infections or bacterial arthritis); and poliomyelitis (a viral disease which may result in the atrophy of muscles, causing permanent deformity); reconstruction after removal of tumors; short stature, such as achondroplasia (a form of dwarfism where arms and legs are very short, but torso is more normal in size); constitutional short stature; and others as may be apparent to those of skill in the art in view of the disclosure herein.

Figure 1:
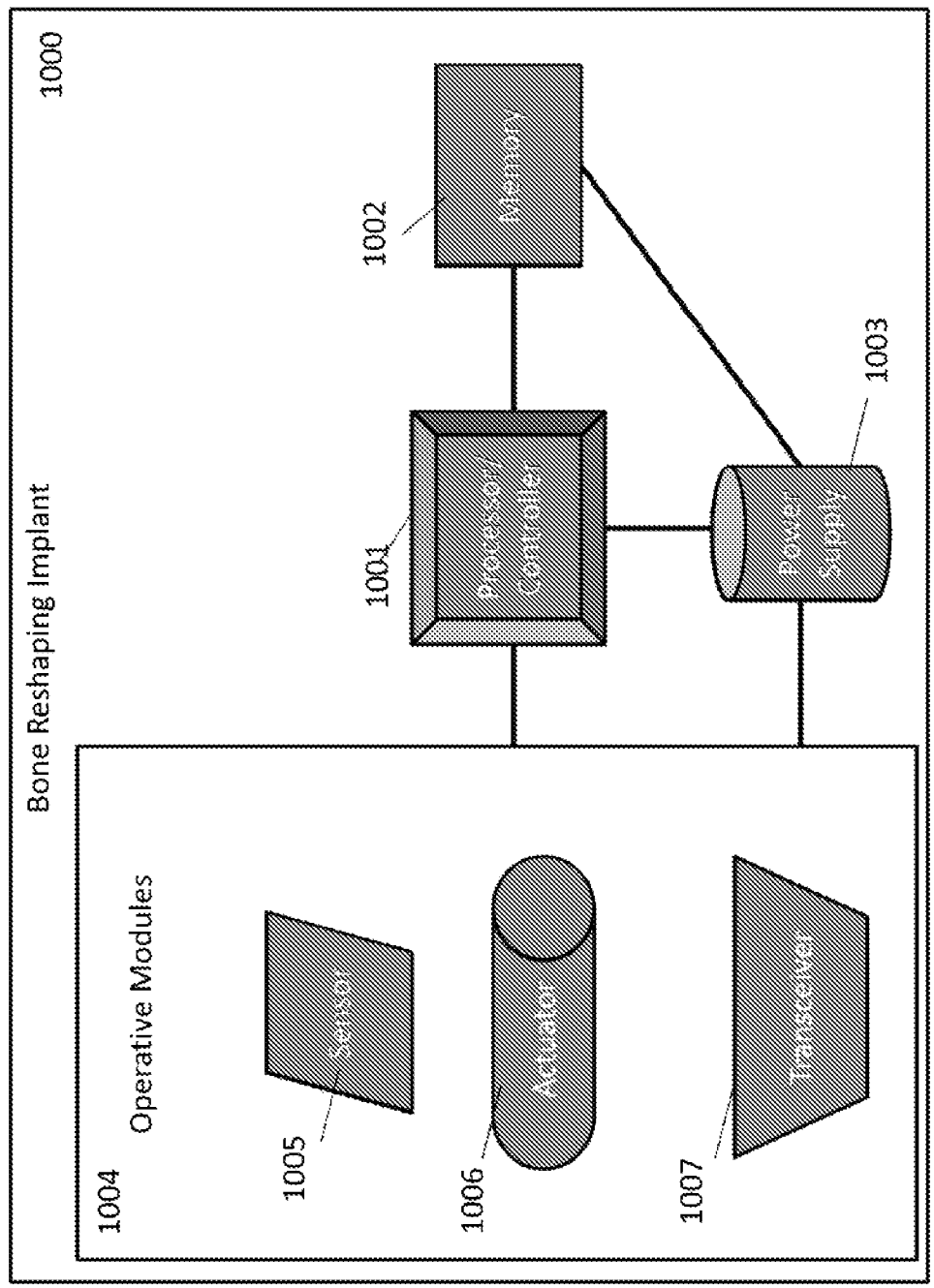
FIG. 1 is a high level schematic of an example bone reshaping implant.

FIG. 1 shows an example high level schematic of a bone shaping implant 1000. Bone shaping implant. 1000 has a number of operative modules 1004. These operative modules may include a sensor 1005, actuator 1006, and transceiver 1007. In some embodiments, the sensor 1005 may be onboard to the implant as illustrated in this example. However, the sensor may also be off-board or adjacent to the processor, which will be later illustrated and described. The sensor 1005 may include: a foil strain gauge; a semiconductor strain gauge; a stress sensor; a pH sensor; a thermometer; a pressure sensor; a displacement sensor (e.g., a film resistor where resistance changes as film is stretched); an electrical conductivity/resistance sensor; an acoustic conductivity resistance sensor; a bio sensor (e.g., a sensor configured to sense the presence or aggregation of platelets, erythrocytes, growth factors, and other biological facilitators of bone healing); and/or any other sensor known in the art for measuring biologically or physiologically relevant data.

These aforementioned sensors may be used to measure parameters that are indicative of a biological condition, such as osteogenesis, ossification, osteoconduction, ostcoinduction, and osteopromotion. In some cases, the measured parameters may indicate a deficiency, such as aplastic anemia, additional bone fractures, brittle bones, or improper bone healing. The measured parameters may also allow the calculation of blood flow, bone mass, bone composition, bone density, bone thickness, bone perfusion, bone strength, and bone oxygenation. The sensors may also be generally configured to measure other biological parameters, such as temperature, pulse, blood flow, blood oxygenation, body composition, respiration, cardiac activity, movement, blood volume, pH, heart-beat, metabolism, and blood composition.

Actuator 1006 may be actuated by a driven magnet system, electrical motor, solenoid/ratchet system, piezoelectric system (e.g., an inchworm motor), shape memory alloy (e.g., Nitol), magnetostrictive elements, gesticulation, and/or any way of driving an actuator known in the art. The movement of the actuator 1006 may drive a modification of the bone shaping implant such as: axial elongation; axial shortening; bending (e.g., deformity correction); twisting (e.g., trauma); expression of active media (e.g., releasing treatment or growth factors); delivery of therapeutic current, ultrasound, radio waves, or magnetic flux across a fracture or bone; delivery of therapeutic compression or vibration across a fracture or bone (e.g., a 1 Hz vibration); any therapeutic delivery of movement, energy, or substances; and/or, any combination of the aforementioned provisions. The active media might include HMG-CoA reductase, epidermal growth factor (EGF), vascular endothelial growth factor (VEGF), fibroblast growth factor (FGF), anti-microbials, and/or antibacterials. More active media that promote bone growth are described in U.S. Patent Pub. 2012/0276205, which is incorporated herein by reference. These active media may be delivered by the actuator 1006, or otherwise administered to a patient to facilitate bone adjustment.

Transceiver 1007 may be configured to communicate with other internal and external components. For example, transceiver 1007 may be configured to send and receive information to an internal sensor, such as sensor 1005. Also for example, transceiver 1007 may transmit/receive data to an external source, such as an external remote control (ERC) device. In some embodiments, transceiver 1007 may transmit data obtained by sensor 1005, processor/control 1001, memory 1002, or any part of the bone reshaping implant 1000 to an external source, such as an ERC. This data may be raw data (e.g., changes in electrical current), measured parameters (e.g., temperature, displacement, or strain), processed information (e.g., a status or biological condition), instructions, interrogatory signals, or any other data, information, or signal relevant to the implant or external device. In some cases, the transceiver 1007 may transmit post action status information to an external device, such as an ERC. For example, such information may include treatment histories, status logs, diagnostic information, recorded data from sensor 1005, and/or data concerning a biological condition.

Transceiver 1007 may also be configured to communicate using Bluetooth (e.g., Bluetooth low energy), ZigBee, Wi-Fi, induction wireless data transmission, medical implant communication service (MICS), radio frequencies, near-field communication (NFC), global system for mobile communications (GSM), or any other form of wireless data transmission.

In certain embodiments, transceiver 1007 may be further configured to communicate directly or indirectly with another external device, such as a data cloud, personal computer, cellular phone, pager, tablet, mobile device, hospital system, or any other device used by a patient or care provider. In some circumstances, it may be desirable for the implant to transmit diagnostic, status, and/or treatment information to a care provider so that the care provider can evaluate the performance of an implantable device, such as implant 1000 and provide recommendations or actually execute therapy to the patient. In some cases, the external device may transmit back to the implant status information, firmware updates, treatment instructions, recommendations, security locks, or other data, information, or protocols relevant to the performance of the implant and/or treatment of the patient.

The operative modules 1004 may be coupled to a processor/controller 1001 to perform operations such as transmitting/receiving data through transceiver 1007, processing sensor data from sensor 1005, controlling actuator 1006, managing system functions, etc. The processor/controller 1001 may also be coupled to memory 1002, which may include volatile and non-volatile memory, and may provide instructions and data to processor/controller 1001. Processor/controller 1001 typically performs logical and arithmetic operations based on program instructions stored within the memory 1002. The instructions in the memory 1002 may be executable to implement the methods described herein. Processor/controller 1001 may also contain or be coupled to a clock for timing therapies.

A power supply 1003 may be coupled to the processor/controller 1001, memory 1002, and/or operative modules 1004 in order to provide operative energy. The power supply 1003 may be a battery, such as a lithium battery, lithium ion battery, nickel-cadmium battery, nickel-metal hydride battery, nickel-hydrogen battery, carbon-zinc battery, silver-oxide battery, zinc-carbon battery, zinc-air battery, mercury oxide battery, alkaline battery, or any other type of battery known in the art and suitable for subcutaneous implantation. Certain batteries may be rechargeable by an external stimulus, or a transient transcutaneous connection. The power supply may also comprise fuel cells, capacitors, inductive coupling, motion powered piezoelectric, motion powered electromagnetic generators, transcutaneous ports (such as ports for hydraulic connections, electrical connections, and other connections to convey power) and/or energy scavenging systems (e.g., systems that use body heat, respiration cycles, body movement, or biochemical reactions). The power supply 1003 may be selected based on factors such as life (e.g., battery life), biocompatibility, power, rechargability, size, current and voltage output, cost, replaceability, the presence or absence of movable parts, and other factors related to performance in an implantable device.

The power supply may also be managed by a power management strategy depending on the power demands. For example, the power management strategy might institute powered, sleep, and idle cycles. In some cases, the power management strategy might take into account the total power and total intended useful life of implant 1000. In some cases, the power management strategy is implemented by the processor/controller 1001.

Figure 2:
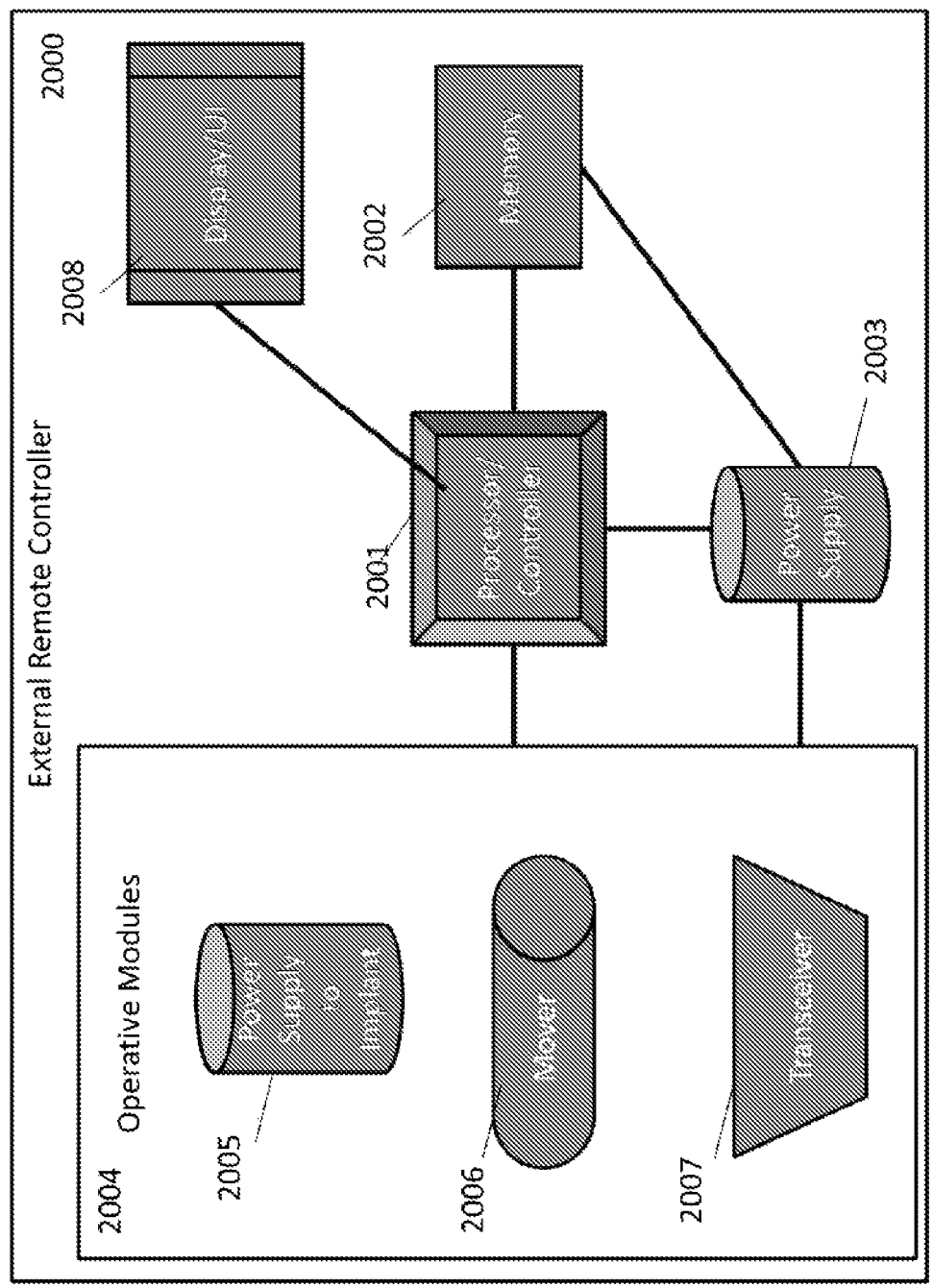
FIG. 2 is a high level schematic of an example external remote controller.

FIG. 2 shows an example high level schematic of ERC 2000. ERC 2000 has a number of operative modules. An optional power supply to implant 2005 may be used to supply power to any part of the implant 1000 including the power supply 1003, the processor 1001, the memory 1002, or any of the operative modules 1004. Power supply to implant 2005 may supply energy through a transcutaneous port, such as transcutaneous ports for electric or hydraulic connections, or any sort of transcutaneous connection (e.g., needle penetration to deliver power or fuel). Power supply to implant 2005 may also supply power by facilitating an energy scavenging system. For example, the bone reshaping implant 1000 may receive power by obtaining energy from body heat, the respiration cycle, body movement, biochemical reactions, and/or any form of energy that may already be available in the human body. Power supply to implant 2005 may escalate those operations to supply more power to the implant 1000. By way of illustration, if implant 1000 received energy from body heat, power to implant may contain a chemical and/or heating apparatus administered to raise the temperature at the location of the implant.

The power supply to implant 2005 may also produce motion, vibrations, electric current, magnetisms, inductance, or capacitance in order to provide power to the implant 1000, which may contain, for example, a motion powered electromagnetic generator, a motion powered piezoelectric motor, coupled inductors, capacitors, batteries, and/or any power supply described in this disclosure or known in the art.

Mover 2006 may cause (e.g., stimulate) bone reshaping implant 1000 to move. For example, mover 2006 may cause actuator 1006 to move by supplying mechanical, electrical, magnetic, capacitive, inductive, or any other type of force or energy to the actuator. Certain illustrative examples of such movement will be discussed further in this disclosure. For example, mover 2006 may include magnets that rotate driven magnets within a telescopic implant. The rotation of mover 2006 causes the implant to lengthen and/or shorten.

Transceiver 2007 is configured to communicate with other internal or external components. For example, transceiver 2007 may transmit or receive information from an implantable device, such as implant 1000. In some embodiments, transceiver 2007 may communicate with an implant's transceiver, such as transceiver 1007, to exchange information including raw data (e.g., changes in electrical current), measured parameters (e.g., temperature, displacement, or strain), processed information (e.g., a status, or biological condition), instructions, interrogatory signals, or any other data, information, or signal relevant to the implant or external device.

In certain embodiments, transceiver 2007 may be further configured to communicate with another external device, such as a data cloud, personal computer, cellular phone, pager, tablet, mobile device, hospital system, or any other device used by a patient or care provider. In some circumstances, it may be desirable for the ERC to transmit diagnostic, status, and/or treatment information to a care provider so that the care provider can evaluate the performance of an implantable device, such as implant 1000, and provide services to the patient. In some cases, the external device may transmit back to the ERC status information, firmware updates, treatment instructions, recommendations, security locks, or other data relevant to the performance of the implant and/or treatment of the patient.

Transceiver 2007 may be configured to communicate using Bluetooth (e.g., Bluetooth low energy), ZigBee, Wi-Fi, induction wireless data transmission, medical implant communication service (MICS), radio frequencies, near-field communication (NFC), global system for mobile communications (GSM), or any other form of wireless data transmission.

The operative modules 2004 may be coupled to a processor/controller 2001 to perform operations such as transmitting/receiving data through transceiver 2007, controlling power supply to implant 2005, controlling mover 2006, managing system functions, etc. The processor/controller 2001 may also be coupled to memory 2002, which may include volatile and/or non-volatile memory, and may provide instructions and data to processor/controller 2001. Processor/controller 2001 typically performs logical and arithmetic operations based on program instructions stored within the memory 2002. The instructions in the memory 2002 may be executable to implement the methods described herein. The processor/controller 2001 may also contain or be coupled to a clock for timing therapies. In some circumstances, the processor/controller 2001 may be programmed to automatically make adjustments to an implant based on programmed data and/or data obtained from the implant.

A power supply 2003 may be coupled to the processor/controller 2001, memory 2002, and/or operative modules 2004 in order to provide operative energy. The power supply 2003 may take any form described in this disclosure (e.g., a similar device as power supply 1003), may plug into an electrical socket, or use any other power or energy supply known in the art.

The power supply 2003 may also be managed by a power management strategy depending on the power demands. For example, the power management might institute powered, sleep, and idle cycles. In some cases, the power management strategy might take into account the total power and total intended useful life of ERC 2000. In some cases, the power management strategy is implemented by the processor/controller 2001.

Additionally, a Display/UI may be onboard or external to ERC 2000. For example, Display/UI 2008 is shown as onboard ERC 2000. However, Display/UI 2008 may also be external and connect to ERC 2000 (e.g., in communication with processor/controller 2001) through wireless or wired data paths, such as high-definition multimedia interface, display port, Bluetooth (e.g., Bluetooth low energy), ZigBee, Wi-Fi, induction wireless data transmission, medical implant communication service (MICS), radio frequencies, near-field communication (NFC), global system for mobile communications (GSM), or any other form of data transmission known in the art. In some embodiments, Display/UI 2008 comprises a touch screen, monitor, television, liquid-crystal display, or any other way of visually showing information. Display/UI 2008 may also include a touch panel, button-selection, keyboard, mouse, voice input, roller ball, gesture interface, or any other way of inputting information known in the art. In some cases, Display/UI 2008 may be coupled to a speaker or sound-producing device that can, for example, play audio data, beep, or sound an alarm.

In some circumstances, it may be desirable for Display/UI 2008 to show measured parameters and/or biological conditions to a care provider. The care provider can then make treatment decisions based on the displayed information. For instance, Display/UI 2008 may show the displacement of sensors attached to the implantable device. If the sensors are attached to two points on a bone, and the sensors move farther apart, this occurrence might suggest that osteogenesis and/or bone lengthening is occurring. The care provider may then increase or decrease the force placed on the bone or the adjustment rate as a result of reviewing this information. In some cases the care provider may directly control the force outputted by the implant. For example, the care provider may send instructions to ERC 2000, which can be uploaded to implant 1000. Alternatively, in some embodiments, the care provider may send instructions directly to implant 1000.

In other embodiments, the care provider can send limits to ERC 2000, where the amount of control that a patient has in adjusting implant 1000 with ERC 2000 is limited to a range of values. For example, the care provider can put in safety cutoffs and/or override features. In some circumstances the care provider or patient can shut down implant operation entirely using an override control, such as if there is an emergency.

In some cases, ERC 2000 may be additionally coupled to an imager, such as an ultrasound, x-ray, magnetic resonance imaging, or computed tomography. In some cases, it may be desired to couple the external remote controller with a portable imager, such as an ultrasound, in order to image the bone region. This information can be displayed with Display/UI 2008 and/or transmitted to an external device for viewing by a user (e.g., a care provider). The images can provide additional information concerning bone healing, therapeutic progression, and/or other clinically relevant data. The additional information can further inform adjustment of a bone reshaping implant.

An illustrative interaction between implant 1000 and ERC 2000 is as follows. Implant 1000 detects a measurable parameter indicative of a biological condition (e.g., using sensor 1005). Implant 1000 then transmits data to ERC 2000

(e.g., continuously, periodically, or in response to interrogation). The data may be raw data for ERC 2000 to process, or data already processed by implant 1000. ERC 2000 can then interpret the data in view of stored patient information and/or display the data to a care provider. The ERC 2000 then transmits instructions to the implant 1000, and the implant 1000 acts in response to those instructions. In some cases, the implant 1000 may also transmit post action status information to ERC 2000, such as a treatment history.

For example, for certain patients undergoing a femoral bone lengthening procedure, the optimal rate of distraction may be approximately 1 mm per day. However, the rate of osteogenesis may vary from patient to patient, as well as the discomfort level associated with different rates of distraction. Feedback recorded by the implant indicative of the rate of osteogenesis may be utilized to optimize the distraction rate for given circumstance. Strain gauge data or other data from on onboard sensor may be utilized to monitor the progress of osteogenesis. That data may be retrieved from the implant by the ERC, which internally, or in combination with clinical personnel, can determine that a particular patient can or should have a reduction in distraction rate to no more than about 0.5 mm per day or no more than about 0.75 mm per day. Alternatively, the implant and control systems disclosed herein, either internally or in combination with clinical staff, may determine in a given instance that the patient might benefit from or is willing to increase the distraction rate to no more than about 1.5 mm or no more than about 2 mm per day.

In addition, the ERC may optionally be provided with a fine tuning adjustment to be made by the patient. This would enable the patient to deviate from the programmed distraction rate by an increase or decrease from the preset rate in an amount of no more than about 5%, in some implementations no more than about 10%, and in other implementations no more than about 25%. Attempts to make adjustments outside of the predetermined bracket limits would have no effect. In this manner, the patient would be given sufficient control to enable fine tuning of the distraction rate to take into account discomfort levels or other desires of the patient.

Figure 3:
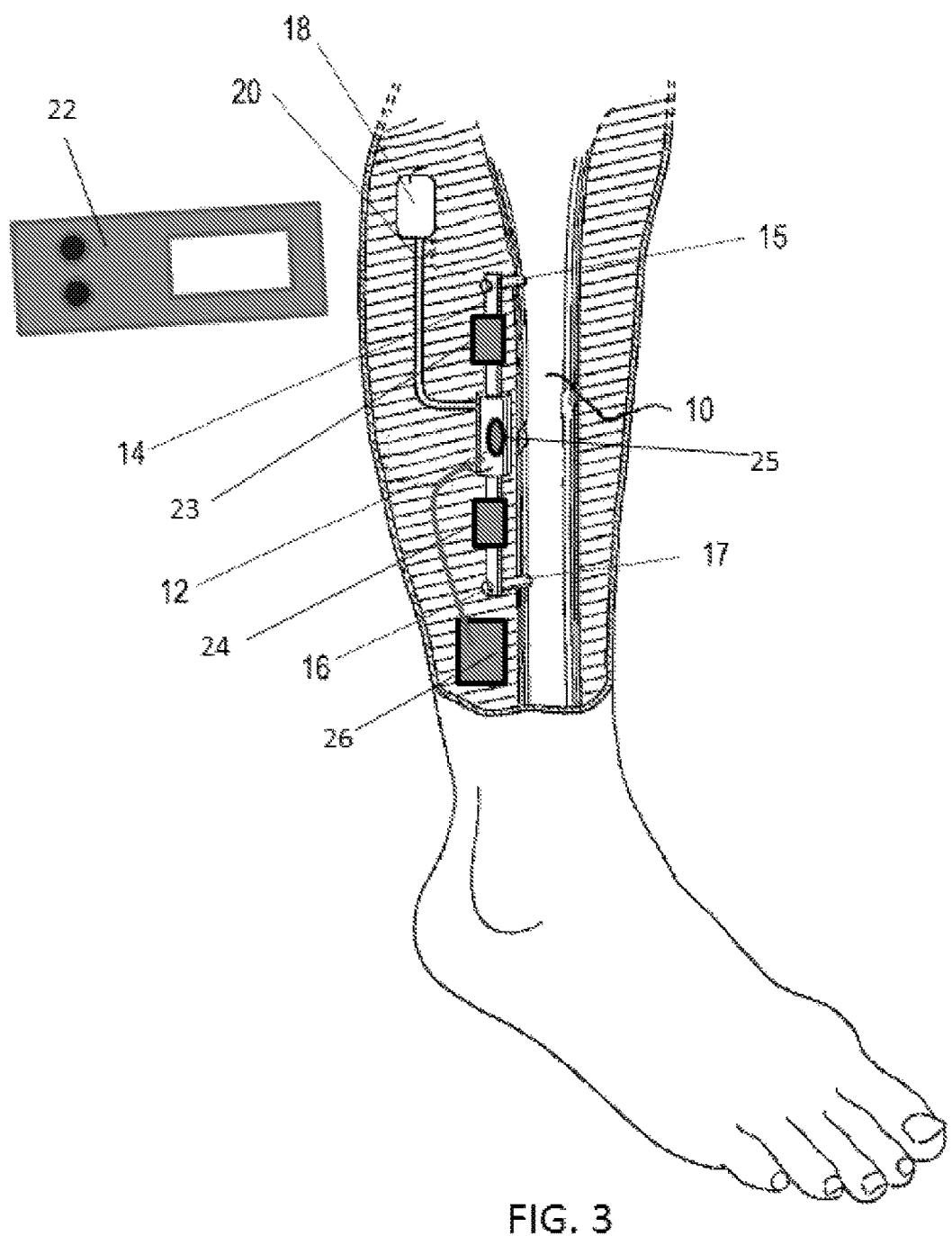
FIG. 3 shows one embodiment illustrating how an implant may attach to a bone and communicate with an external remote controller.

FIG. 3 illustrates one embodiment. The unmodified tibia 10 has a bone reshaping implant 12 attached thereto. The bone reshaping implant 12 may be configured for axial expansion or compression, and/or torsion or other movement necessary to achieve the desired clinical result.

Bone reshaping implant 12 is provided with at least a first attachment point 14 and a second attachment point 16 for attachment to the bone 10. In the illustrated embodiment, first and second attachment points 14 and 16 may be apertures for receiving a first bone screw 15 and a second bone screw 17. Attachment of the implant 12 to the bone 10 may be accomplished in any of a variety of ways, such as by utilizing one or two or more bone screws at each of the first and second attachment points. Alternatively, the first and second attachment points may be connected to a plate, adhesively secured to the bone, secured to a collar or ring which surrounds at least a portion or potentially encircles the bone, or other attachment structure having sufficient structural integrity to achieve the desired clinical result.

The portion of bone located between the first bone screw 15 and second bone screw 17 is the treatment zone, over which forces generated by the bone reshaping implant 12 will be distributed. Although not illustrated, the bone 10 in between the first bone screw 15 and second bone screw 17 will normally contain one or more bone deformities, the correction of which is desired. Also not pictured, the bone 10 in between the first bone screw 15 and second bone screw 17 may contain a bone injury, such as a fracture.

One or more sensors 23 and 24 may be provided. The one or more sensors may be fixed to a location on the implant body 12. The sensors may also be desirably located on the connection points 15 and 17, or to locations in contact with the bone. The sensors 23 and 24 are configured to measure a parameter indicative of a biological condition (e.g., osteogenesis or any of the biological conditions described in this disclosure). They may also be of any type (or combination of any type) described in this disclosure or known in the art. For example, in the particular configuration illustrated, the two sensors 23 and 24 may sense stress (strain gauge) or a distance between each other using, for example, light such as infrared (IR) light, lasers, electric current, inductance, film resistors, acoustics, or any other way of measuring distance between objects known in the art. This distance measurement may be correlated to ostegenesis. For example, if the sensors are moving farther away from each other, successful osteogenesis may be occurring, thereby lengthening the distance between the sensors.

Processor 25 may interpret the outputs of the sensors to calculate a measured parameter. For example, in measuring a strain on the bones, sensors 23 and 24 may output an electric current that is correlated with strain. Processor may then calculate the strain based on those electrical outputs. Additionally processor 25 may also compile data obtained by sensors (e.g., strain over time and/or the different parameters measured by sensors) for a biological conclusion. For example, by factoring pH, temperature, strain, and displacement, the processor 25 may determine whether osteogenesis is occurring and also an indicium of the rate and circumferential regularity or irregularity of osteogenesis. Processor 25 may additionally calculate an amount of force, an amount of increased force, or an amount of decreased force that could be applied to the bone for effective therapeutic treatment or increasing efficacy of treatment.

In some embodiments, the processor 25 may control a modification of treatment. For example, the processor 25 may drive an actuator coupled to the implant body 12, where the actuator may change the amount or angle of force applied to the bone. For example, implant body 12 may contain motors, magnetic coils, and/or elastic members that contract or expand the implant body 12. The contraction may put more compressive force on at least one side of the bone, whereas the expansion may put more distractive force on at least one side of the bone. In either case, the implant body 12, because of its location on one side of the bone, may also put an angular force on the bone.

One or more transceivers 18 may also be provided. The transceiver 18 may be in communication with the bone reshaping implant 12 or the one or more sensors 23 and 24 by a cable 20, or in other embodiments, wirelessly. Transceiver 18 may alternatively be within, or carried by, the implant. Cable 20 may include electrical, optical, fluid, or other conduit, depending upon the functionality of the implant. The transceiver 18 may be configured for transmitting and receiving information. For example, the transceiver 18 may be configured to communicate to an external device using any of the modalities previously mentioned, such as induction wireless data transmission or any other form of wireless data transmission. In some embodiments, the transceiver 18 is configured to transmit data to ERC 22. The data may be data generated by sensors 23 and 24, data outputted by the processor 25, status information, a biological condition, a request for information from an external device, or any other relevant information described in this disclosure.

In some embodiments, transceiver 18 may be configured to transmit data continuously. Such continuous transmission might be desirable in order to allow an external remote control to monitor the patient's conditions and undertake reactive measures when necessary. However, in some circumstances, continuous transmission may require more power, and could lead to low battery life for the implantable device. In other embodiments, transducer 18 may be configured to transmit data periodically, such as every minute, every hour, every day, every week, every month, every year, and/or any period of time, including any time between any two of the aforementioned periods of time. In other embodiments, transceiver 18 may be configured to transmit data in response to an interrogation signal by an ERC 22 or some other external device. In still other embodiments, transceiver 18 may be configured to transmit data in response to an event, for example a sudden change in a measured parameter, reaching a preset trigger threshold in a measured parameter, a detected biological condition, or a change in implant status (e.g., damage to the implant or the implant is out of batteries).

Transceiver 18 may also be configured to receive data transmitted from an ERC 22. This data may contain instructions, such as directions for the processor to drive the actuator. It may also provide a status or request for the transceiver to send data. It may also provide firmware updates and/or updates to algorithms, protocols, or therapies.

In some embodiments, a power supply 26 may also be provided. The power supply 26 may be a battery or any power supply discussed in this disclosure. Power supply may be carried within or on the implant 12, or near the implant as illustrated.

In some embodiments, a memory may be coupled to processor 25 in order to store, for example, processor data, firmware, instructions, power management data, and information to be outputted by the transceiver on interrogation.

ERC 22 may be an ERC with the same functionalities as ERC 2000. In particular, ERC 22 may be in communication with transceiver 18 to receive data from the implant and send responsive instructions to the implant. In some cases, the implant acts in response to ERC 22's instructions. For example, ERC 22's instructions may cause an actuator coupled to implant body 12 to actuate.

Figure 4:
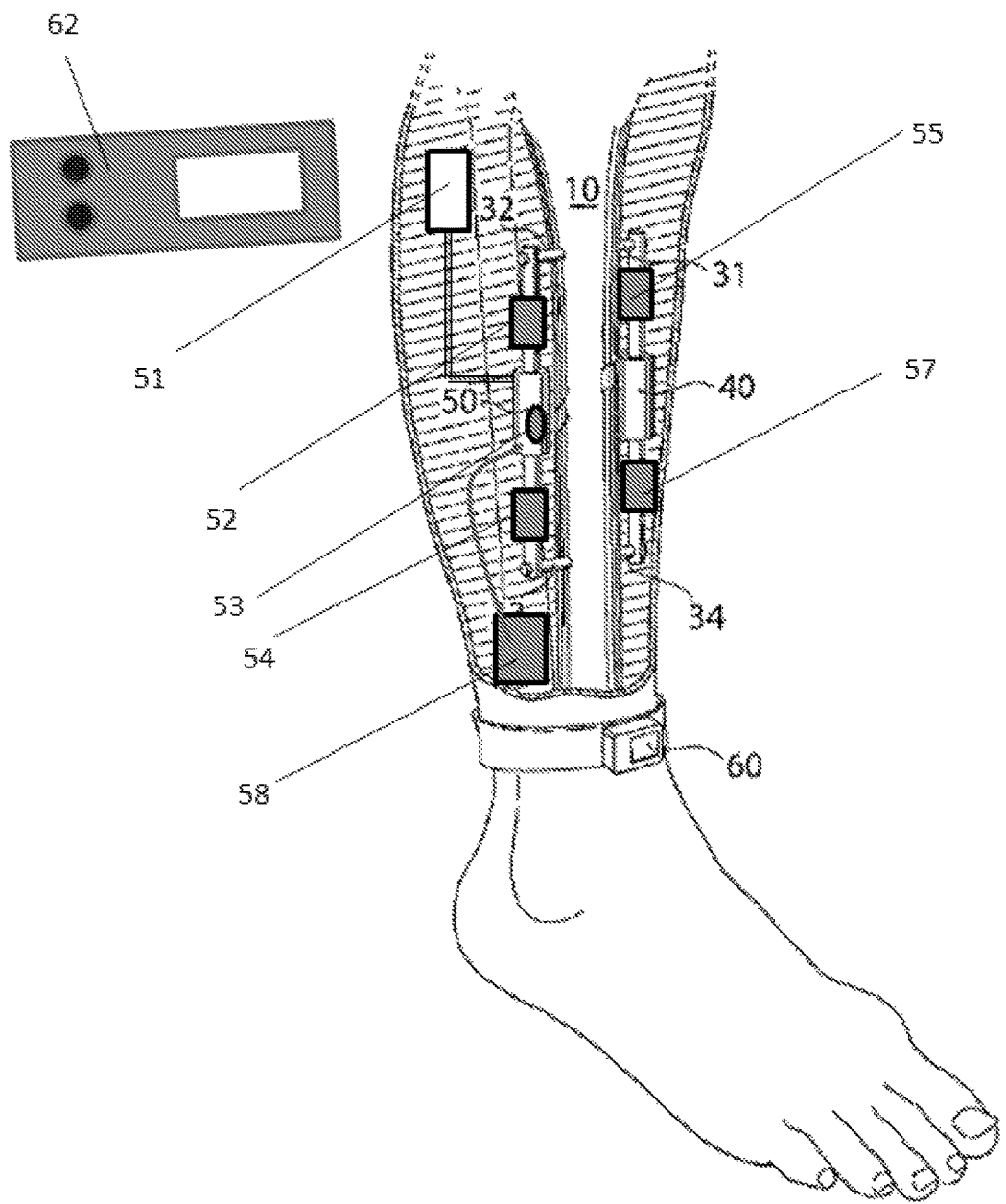
FIG. 4 shows another embodiment illustrating how an implant may be attached to two sides of a bone and may also be in communication with an external remote controller.

FIG. 4 illustrates another embodiment. This embodiment has two bone reshaping implant bodies 40 and 50. In some embodiments, each of implant body 40 and 50 may be coupled to its own sensors. For example, implant body 40 has sensors 55 and 57, and implant body 50 has sensors 52 and 54. There may be one or more internal or external power supply 58 as desirable to power the implants. There may also be one or more internal or external transceiver 51 as desirable to transmit and receive information for the implant bodies 40 and 50. There may also be one or more processors 53 as desirable to process data.

Having two (or more) implants, such as implants 40 and 50, on a bone may be desirable in certain situations in order to better support the bone structure. These implants may be operated jointly or independently, depending on therapeutic applications. For example, two implants putting the same pressure in the same direction on the bone simultaneously from two sides may prevent or tend to correct curvature and/or other deformities to bones during osteogenesis. On the other hand, to improve bone curvature, further angular force may be placed on a bone by compressing one implant and distracting the other, and/or applying different forces to the different implants. In still another application, osteogenesis may occur, in some circumstances, at different rates across a bone. Using multiple implants can compensate for these bone growth differences by applying compensatory compression or distraction therapies.

It should be appreciated that there may be many configurations in which one or more implant may be fixed to bones. For example, there are configurations in the art using four or more implant bodies attached to a femur or spine at various points. Embodiments of the present disclosure are not limited to any particular formation or way of attaching implants to bones.

Figure 5:
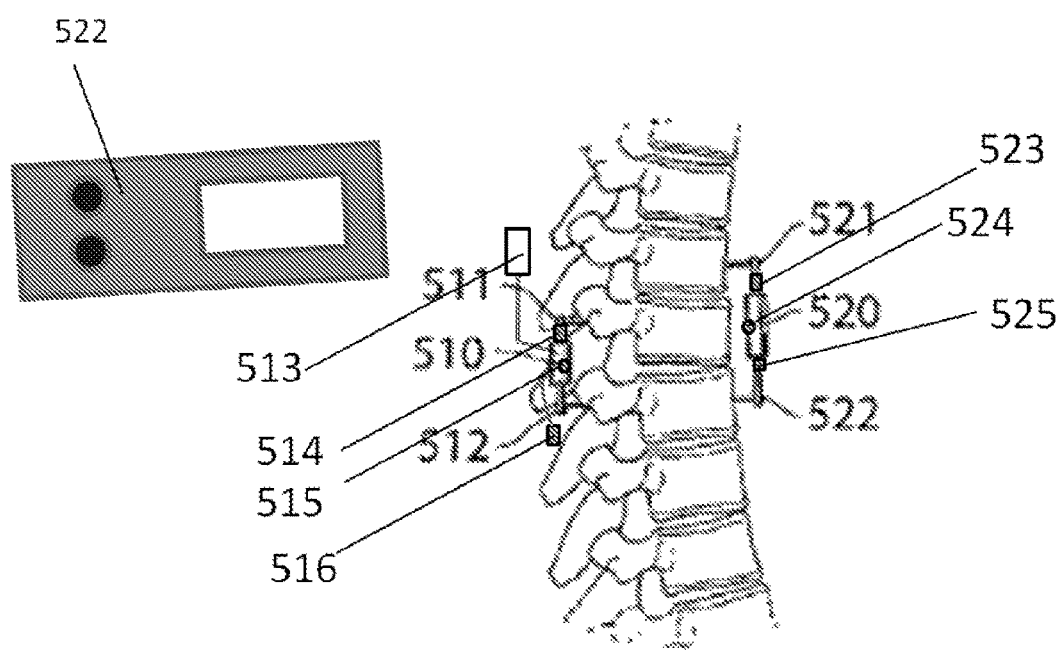
FIG. 5 shows another embodiment illustrating how an implant may be attached to vertebrae and may also be in communication with an external remote controller.

FIG. 5 illustrates that similar implantable devices may be placed in other parts of the body. For example, one or more implantable devices 510 and 520 may be implanted along the spine in order to adjust the curvature of the spine. For illustrative purposes implant 510 is shown attached to two adjoining vertebrae by two anchoring devices 511 and 512, whereas another device 520 is shown typically in a separate procedure (both illustrated on the same bone for convenience) attached to non-adjoining vertebrae by two anchoring devices 521 and 522. This embodiment can be used to adjust the curvature of the spine, such as to relieve a herniated lumbar disc or the like.

Figure 6:
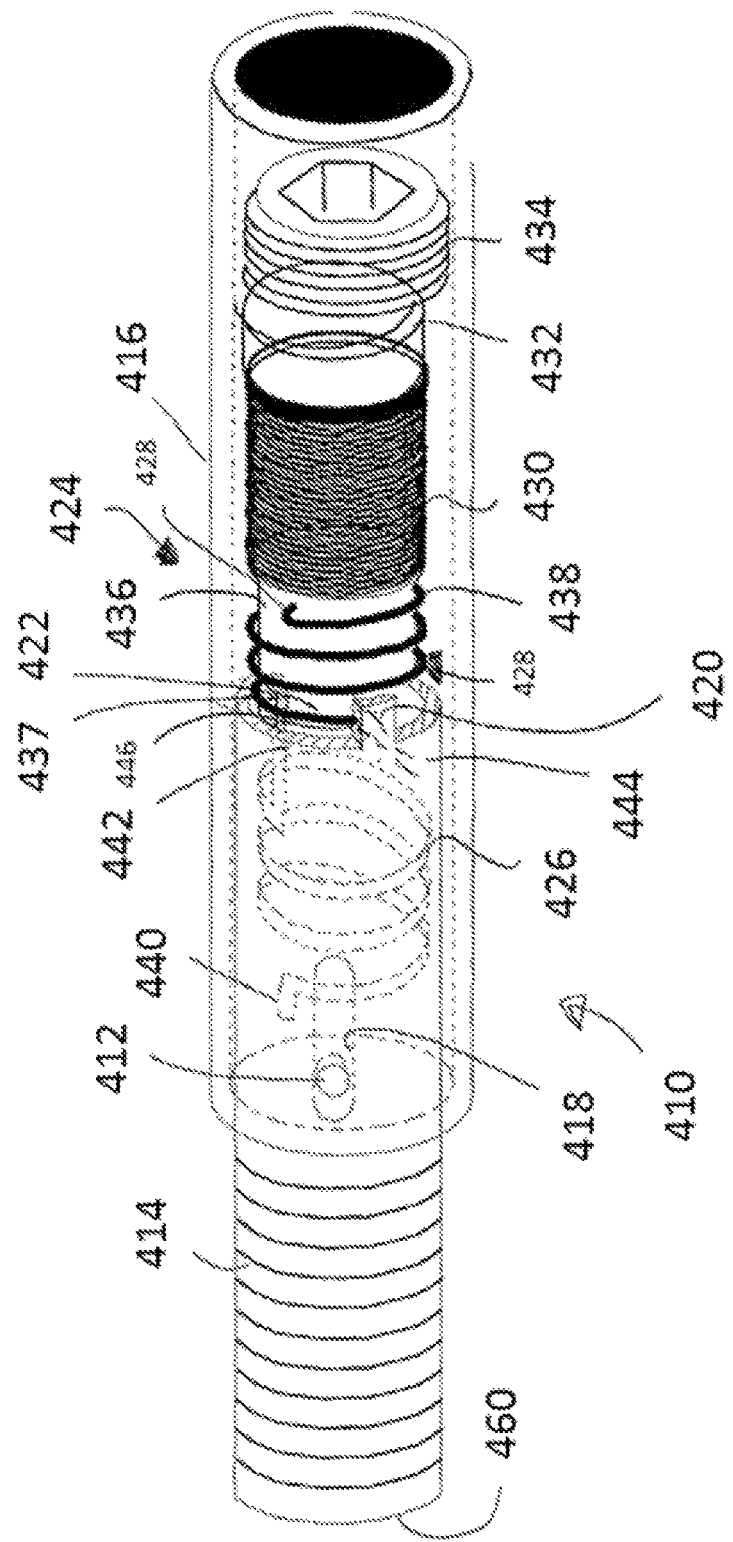
FIG. 6 is an example of an implantable device that can be adjusted by external stimulus.
Figure 7:
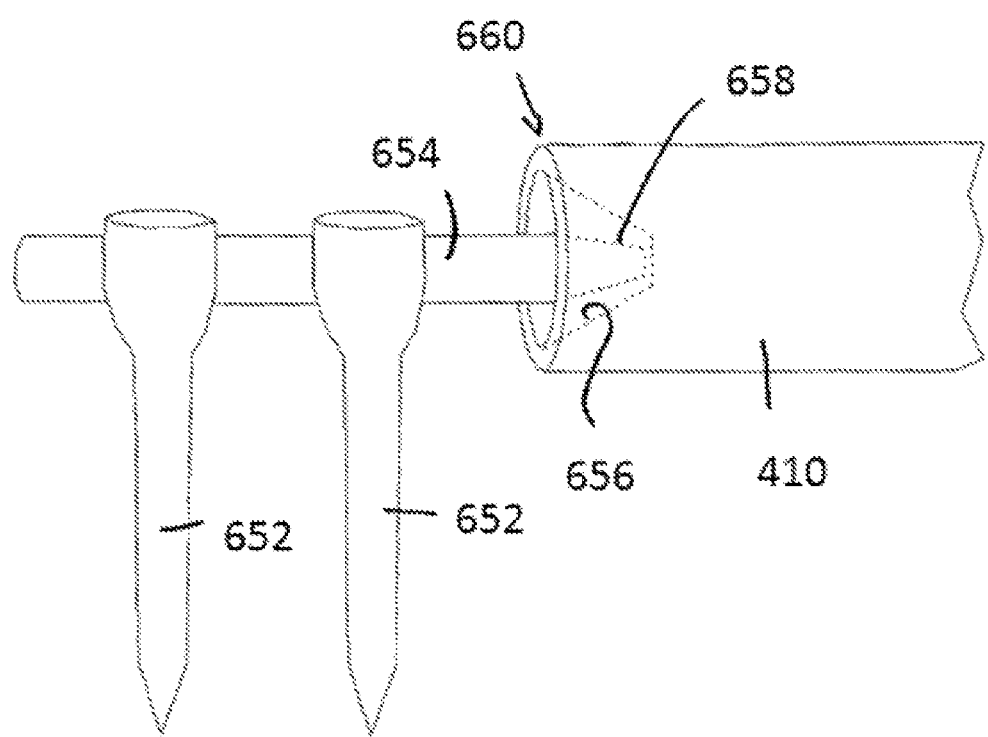
FIG. 7 is an example of how an implantable device may be attached to a bone using screws.

In some embodiments, the implant is configured to be adjusted externally. For example, FIG. 6 shows an expanding or telescopic rod 410. The opposing ends of rod 410 are fixed to selected positions on the bone using conventional surgical screws. For example, rod 410 may be fixed to a bone using screws 542 as depicted in FIG. 7 or FIG. 3. Additionally, or alternatively, rod 410 may be used as an intermedullary implant, or as part of or in conjunction with implants 12, 40, 50, 510, and/or 520. In this way, it should be appreciated, that the externally controlled adjustments to rod 410 can be made based on measured parameters indicating biological conditions. For example, the sensors of implants 12, 40, 50, 510, and/or 520 can transmit relevant data or information, as described in this disclosure, to an ERC. The ERC, or a care provider, can use the information to determine if the ERC should adjust the implant.

The rod 410 may produce a controlled force, slowly over time, under precise external control, and be isolated or implanted completely under the skin and protected by the natural barrier, which the skin provides. Rod 410 may also be small, powerful, simple enough to be readily manufactured, immune to accidental activation, and biologically inert.

The pick-up coil 430 receives energy from an external hand-held source of energy, such as a low frequency generator of electromagnetic radiation, which is brought into proximity with coil 430. Some examples of such a hand-held source of energy are ERC 22, 62, and/or 522. Rod 410 is implanted beneath the skin barrier, while the source of energy is exterior to the body. The external inductive power source may be driven at conventional line frequency. In the event that the coil 430 is to be able to efficiently drive the muscle wire 438, then either a storage capacitor with a control diode can be added in circuit with coil 430, or with more complexity, a battery with a diode voltage multiplier, and control diode could be used. Any means of impedance matching between coil 430 and wire 438 on one hand and between coil 430 and the inductive power source on the other may be employed. The use of external power sources and inductively powered implanted coils is well known to the art and are routinely used, for example, in charging implanted pacemaker devices.

In some alternatives, energy can be fed into the pick-up coil until enough is stored in the capacitor to drive the motor 428. Upon the firing of the motor 428, the hand-held device could sense the discharge, and shut-off for the prescribed lock-out period. In other alternatives, an on-board battery or power supply assists in charging the capacitor, and thus requires significantly more control electronics. For example, such an onboard battery or power supply may be power supply 26, 58, and/or 516.

In certain embodiments and alternatives, an internal processor, such as processors 25, 53, and/or 515 may additionally control the power supply and/or motor 428, such as by enabling or disabling the extension/contraction of rod 410, or by placing limits on such extension/contraction. The processor may also process further instructions, data, statuses, etc, from an ERC.

Figure 8:
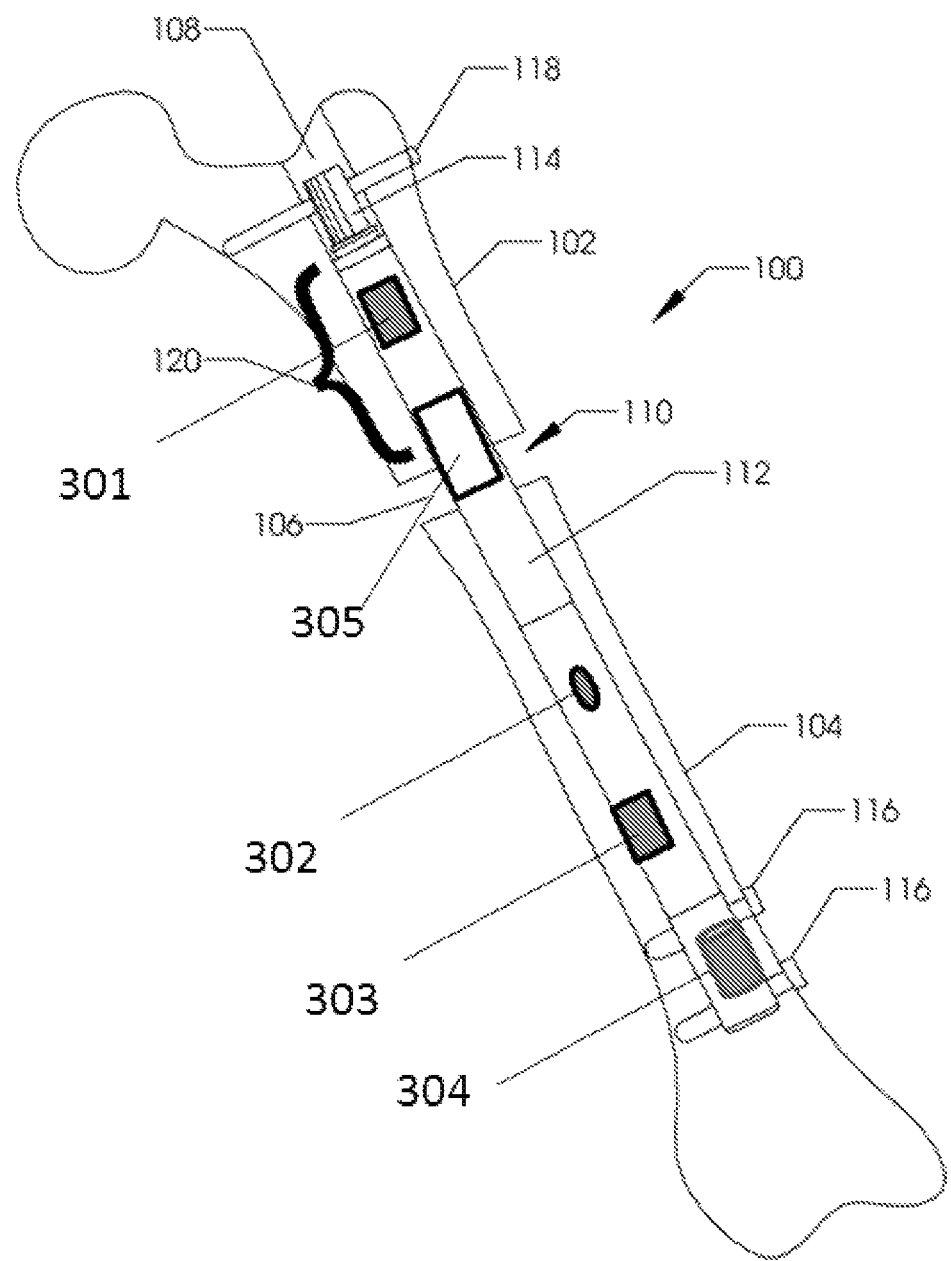
FIG. 8 illustrates an example embodiment having an implantable intramedullary device.

In some cases, an implant may be placed inside a bone, such as inside the medullary canal. FIG. 8 shows such an implant 110, placed inside a bone. The implant has at least one, and in the illustrated implementation two sensors 301 and 303 such as strain gauges or other disclosed elsewhere herein, coupled to the implant body. It also has processor 302, power supply 304, and transceiver 305.

FIG. 9 further details one particular implant 110 and how it actuates. The implant 110 has one or more distraction shaft screw holes 122 in the distraction shaft 114 through which the screws may be placed. Likewise, the housing 112 is attached to an end cap 130 which has one or more housing screw holes 124 through which the screws may be placed. FIG. 10a shows that the housing 112 of the intramedullary lengthening device 110 includes a magnet housing 128 and splined housing 126. The housings 126, 128 may be attached to each other by means of welding, adhesive bonding, or other joining techniques. The magnet housing 128 is sealability closed at one end (the end opposite the interface with the splined housing 126) by the attachment of the end cap 130. The end cap 130 may be attached to the magnet housing 128 by means of welding, adhesive bonding, or other joining techniques. In use, the distraction shaft 114 is driven from the housing 112 by means of a lead screw 136 which turns inside a nut 140 that is secured to an inner surface adjacent to a cavity 137 of the distraction shaft 114. The lead screw 136 is mechanically coupled, in an indirect manner, to cylindrical permanent magnet 134 contained within the magnet housing 128. Rotation of the cylindrical permanent magnet 134, which is magnetically driven by an external adjustment device 180 (FIG. 11), effectuates rotation of the lead screw 136.

Cylindrical magnet 134 is fixedly contained within a magnet casing 158 using, for example, an adhesive such as an epoxy. The magnet casing 158 rotates relative to the magnet housing 128. The cylindrical magnet 134 may be a rare earth magnet such as Nd—Fe—B and may be coated with Parylene or other protective coatings in addition to being protected within the magnet casing 158, for example hermetically potted with epoxy. The magnet casing 158 contains an axle 160 on one end which attaches to the interior of a radial bearing 132. The outer diameter of the radial bearing 132 is secured to the interior of a radial bearing 132. The outer diameter of the radial bearing 132 is secured to the interior of the end cap 130. This arrangement allows the cylindrical magnet 134 to rotate with minimal torsional resistance. At its other, opposing end, the magnet housing 158 includes an axle 161, which is attached to a first planetary gear set 154. Shown in FIG. 10b, the axle 161 includes the sun gear of the first planetary gear set 154, the sun gear turning the planetary gears of the first planetary gear set 154. The first planetary gear set 154 serves to reduce the rotational speed and increase the resultant torque delivery from the cylindrical magnet 134 to the lead screw 136. A second planetary gear set 156 is shown between the first planetary gear set 154 and the lead screw 136, for further speed reduction and torque augmentation. The number of planetary gear sets and/or the number of teeth in the gears may be adjusted, in order to achieve the desired speed and torque delivery. For example, a lead screw with eighty (80) threads per inch attached to two planetary gear sets of 4:1 gear ratio each inside a 9 mm device with magnet location in the distal femur can achieve at least 100 lb. of distraction force at a greater than average distance or gap from the external device.

Figure 12:
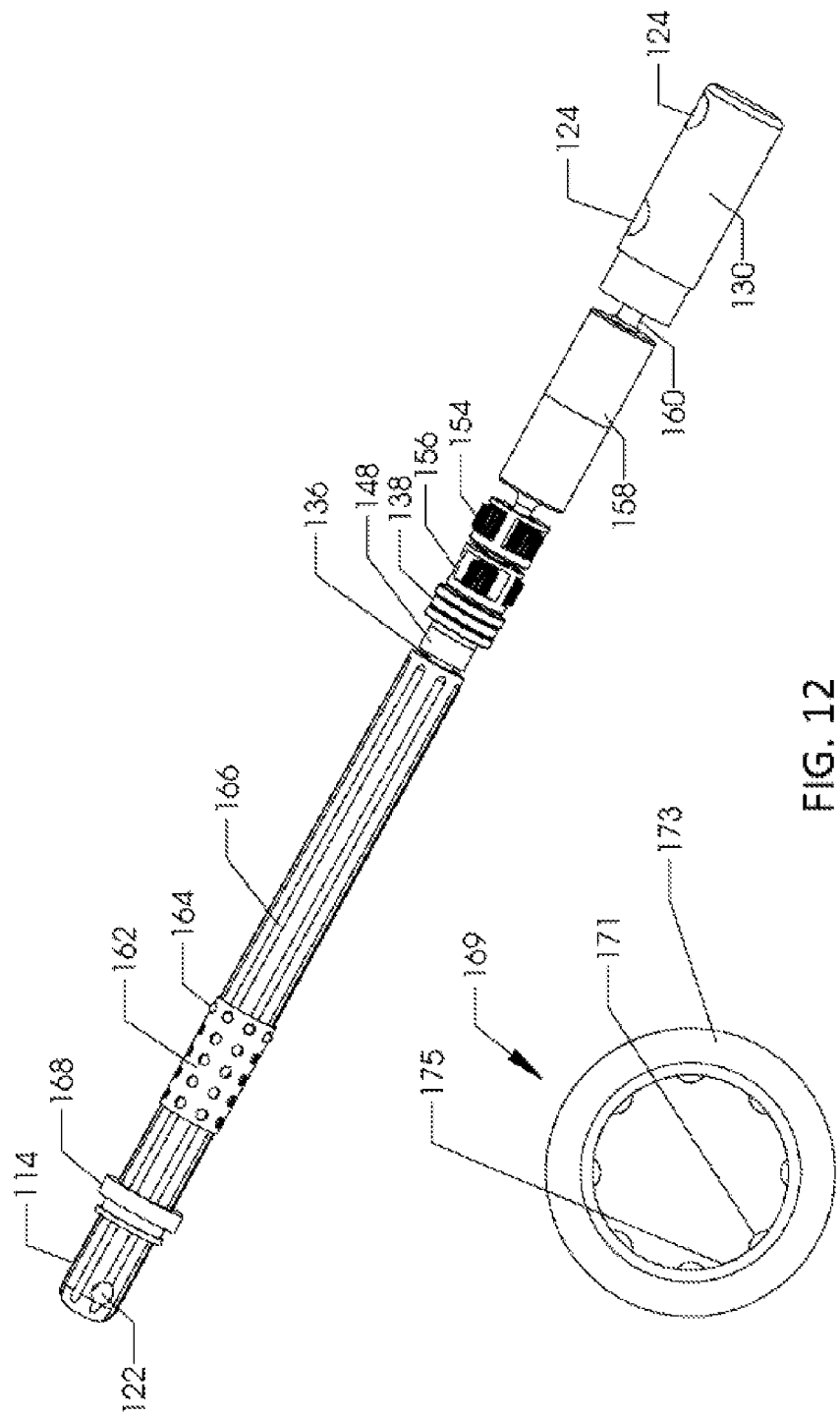
FIG. 12 illustrates a perspective view of some of the internal components of the device of FIG. 9.

In FIG. 12, the housing components have been remove to reveal various internal features, including a collar that allows sliding of the distraction shaft 114 within the housing 112, and which also keeps the distraction shaft 114 from being able to rotate within the housing 112. This allows full stability of the bone 100.

FIG. 11 illustrates an example of an ERC 180 which is used to non-invasively control the bone reshaping implant 110 by means of a magnetic coupling which transmits torque. ERC 180 comprises a magnetic handpiece 178 (e.g., a mover), a control box 176 (containing a processor), which may be integrated with the handpiece, and a power supply 174 such as a battery or external plug for connection to a standard power outlet. The control box 176 includes a control panel 182 having one or more controls (buttons, switches or tactile, motion, audio or light sensors) and a display 184. The display 184 may be visual auditory, tactile, the like, or some combination of the aforementioned features, or any other display/UI described in this disclosure. The control box 176 may further contain a transceiver for communication with transceiver 305 of the implant and/or other external devices. With implant 110, the transceiver may obtain or send information including raw data (e.g., changes in electrical current), measured parameters (e.g., temperature, displacement, or strain), processed information (e.g., a status, or biological condition), instructions, interrogatory signals, or any other data, information, or signal relevant to the implant or external device. With another external device, ERC 180 may send and receive, for example, diagnostic, status, treatment information, and/or any data obtained from the implant to a care provider so that the care provider can evaluate the performance of an implantable device, such as implant 110, and provide services to the patient.

The ERC 180 may also be programmed and/or implement protocols based on data obtained from the implant. For example, ERC 180 (or a care provider) may determine that the rate of compression or distraction should be slowed or accelerated, and adjust the implant accordingly. Alternatively, the ERC may display an appropriate adjustment for the patient to input or cause the ERC to transmit to the implant. Additionally, in some circumstances, ERC 180 may limit a user's ability to make adjustments to therapy depending on therapeutic limits.

A person/one having ordinary skill in the art would further appreciate that any of the various illustrative logical blocks, modules, processors, means, circuits, and algorithm steps described in connection with the aspects disclosed herein may be implemented as electronic hardware a digital implementation, an analog implementation, or a combination of the two, which may be designed using source coding or some other technique), various forms of program or design code incorporating instructions (which may be referred to herein, for convenience, as "software" or a "software module"), or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

The various illustrative logical blocks, modules, and circuits described in connection with the aspects disclosed herein and in connection with the figures may be implemented within or performed by an integrated circuit (IC), an access terminal, or an access point. The IC may include a general purpose processor, a digital signal processor (DSP), an application specific integrated circuit. (ASIC), a field programmable gate array (FPGA) or other programmable logic device, discrete gate or transistor logic, discrete hardware components, electrical components, optical components, mechanical components, or any combination thereof designed to perform the functions described herein, and may execute codes or instructions that reside within the IC, outside of the IC, or both. The logical blocks, modules, and circuits may include antennas and/or transceivers to communicate with various components within the network or within the device. A general purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration. The functionality of the modules may be implemented in some other manner as taught herein. The functionality described herein (e.g., with regard to one or more of the accompanying figures) may correspond in some aspects to similarly designated "means for" functionality in the appended claims.

If implemented in software, the functions may be stored on or transmitted over as one or more instructions or code on a computer-readable medium. The steps of a method or algorithm disclosed herein may be implemented in a processor-executable software module which may reside on a computer-readable medium. Computer-readable media includes both computer storage media and communication media including any medium that can be enabled to transfer a computer program from one place to another. A storage media may be any available media that may be accessed by a computer. By way of example, and not limitation, such computer-readable media may include RAM, ROM, EEPROM, optical disk storage, magnetic disk storage or other magnetic storage devices, or any other medium that may be used to store desired program code in the form of instructions or data structures and that may be accessed by a computer. Also, any connection can be properly termed a computer-readable medium. Combinations of the above should also be included within the scope of computer-readable media. Additionally, the operations of a method or algorithm may reside as one or any combination or set of codes and instructions on a machine readable medium and computer-readable medium, which may be incorporated into a computer program product.

It is understood that any specific order or hierarchy of steps in an disclosed process is an example of a sample approach. Based upon design preferences, it is understood that the specific order or hierarchy of steps in the processes may be rearranged while remaining within the scope of the present disclosure. The accompanying method claims present elements of the various steps in a sample order, and are not meant to be limited to the specific order or hierarchy presented.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the claims, the principles and the novel features disclosed herein. The word "example" is used exclusively herein to mean "serving as an example, instance, or illustration." Any implementation described herein as "example" is not necessarily to be construed as preferred or advantageous over other implementations.

Certain features that are described in this specification in the context of separate implementations also can be implemented in combination in a single implementation. Conversely, various features that are described in the context of a single implementation also can be implemented in multiple implementations separately or in any suitable sub-combination. Moreover, although features may be described above as acting in certain combinations and even initially claimed as such, one or more features from a claimed combination can in some cases be excised from the combination, and the claimed combination may be directed to a sub-combination or variation of a sub-combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the implementations described above should not be understood as requiring such separation in all implementations, and it should be understood that the described program components and systems can generally be integrated together in a single software product or packaged into multiple software products. Additionally, other implementations are within the scope of the following claims. In some cases, the actions recited in the claims can be performed in a different order and still achieve desirable results.

What is claimed is:

1. A bone growth device comprising:
   an implant body;
   an actuator coupled to the implant body;
   a sensor disposed adjacent to the implant body configured to detect a measurable parameter indicative of a biological condition;
   a transceiver configured to transmit data associated with the measureable parameter to an external remote control and receive instructions from the external remote control;
   a memory disposed within the implant body; and
   a controller coupled to the memory and configured to adaptively adjust the actuator in response to the measurable parameter detected by the sensor, information stored in the memory, and the instructions received from the external remote control, wherein the actuator adjusts the implant body.

2. The device of claim 1, wherein the information the memory is configured to store comprises at least one of data associated with the measureable parameter, data associated with the instructions received from the external remote control, and status information.

3. The device of claim 1, wherein the implant body further comprises a first connection point between the implant body and a first portion of bone, and a second connection point between the implant body and a second portion of bone.

4. The device of claim 3, wherein the adjustment comprises applying compression between the first connection point and the second connection point.

5. The device of claim 3, wherein the adjustment comprises applying a force to the bone which has at least a component which is non-parallel to a straight line extending through a first attachment point and a second attachment point.

6. The device of claim 3, wherein the adjustment comprises applying force to lengthen the distance between a first attachment point and a second attachment point.

7. The device of claim 1, wherein the biological condition is osteogenesis.

8. The device of claim 3, wherein the measureable parameter is a distance between the first connection point and the second connection point.

9. The device of claim 3, wherein the measureable parameter is a motion between the first connection point and the second connection point.

10. The device of claim 1, wherein the measureable parameter is at least one of blood flow, temperature, strain, pH, stress, bone composition, bone mass, bone density, bone thickness, bone perfusion, bone strength, bone oxygenation, electrical conductivity, and a presence of active media.

11. The device of claim 1, further comprising a power supply.

12. The device of claim 11, wherein the power supply is configured to be charged by the external remote control.

13. The device of claim 1, further comprising an energy receiving element configured to receive energy from an external source.

14. The device of claim 1, wherein the implant body is an intramedullary device.

15. An external remote control for a bone growth device, comprising:
    a first transceiver configured to receive data associated with a measurable parameter indicative of a biological condition from the bone growth device and to transmit treatment instructions for the bone growth device;
    an input for receiving care information from a care provider; and
    a controller configured to:
    receive the data associated with a measurable parameter and care information,
    generate the instructions for the bone growth device based on the data associated with a measurable parameter and the care information.

16. The external remote control of claim 15, wherein the input comprises a second transceiver configured to transmit patient information to a care provider and receive care information from the care provider.

17. The external remote control of claim 16, wherein the first transceiver and the second transceiver are one transceiver.

18. The external remote control of claim 15, wherein the care information from a care provider is the instructions.

19. The external remote control of claim 15, further comprising a display configured to display patient information.

20. The external remote control of claim 15, wherein the input is a user interface.

21. The external remote control of claim 15, further comprising an energy transmitter configured to supply power to the bone growth device.

22. The external remote control of claim 15, further comprising a mover configured to actuate the bone growth device.

23. The external remote control of claim 22, wherein the mover utilizes at least one of magnets, heat, and electric current to actuate the bone growth device.

24. The external remote control of claim 15, further comprising a memory configured to store at least one of the data associated with a measureable parameter, the care information, and the instructions.

25. A method of treating a patient using an implantable device, comprising the steps of:
    measuring a measurable parameter indicative of a biological condition using the implantable device;
    processing the measurable parameter using a controller disposed in the implantable device;
    transmitting data associated with the measureable parameter from the implantable device to an external remote control;
    transmitting instructions from the external remote control to the implantable device; and
    adjusting the implantable device in response to the measurable parameter, treatment information stored in memory in the implantable device, and the instructions received from the external remote control.

26. A method of treating a patient as in claim 25, wherein measuring a measurable parameter comprises measuring compression between a first portion of bone and a second portion of bone.

27. A method of treating a patient as in claim 25, wherein measuring a measurable parameter comprises measuring a distance between a first portion of bone and a second portion of bone.

28. A method of treating a patient as in claim 25, wherein the measurable parameter comprises measuring motion between a first portion of bone and a second portion of bone.

29. The device of claim 25, wherein the biological condition is osteogenesis.

30. The device of claim 25, wherein the actuation further comprises receiving actuation energy from the external remote control.

* * * * *